United States Patent
Sheng

(10) Patent No.: US 9,808,309 B2
(45) Date of Patent: Nov. 7, 2017

(54) ELECTROCAUTERY INSTRUMENT FOR ENDOSCOPIC THERAPY

(71) Applicant: GETAC TECHNOLOGY CORPORATION, Hsinchu County (TW)

(72) Inventor: Yen-Long Sheng, Taipei (TW)

(73) Assignee: Getac Technology Corporation, Hsinchu County (TW)

( * ) Notice: Subject to any disclaimer, the term of this patent is extended or adjusted under 35 U.S.C. 154(b) by 735 days.

(21) Appl. No.: 14/464,575

(22) Filed: Aug. 20, 2014

(65) Prior Publication Data

US 2016/0051310 A1 Feb. 25, 2016

(51) Int. Cl.
*A61B 18/14* (2006.01)
*A61B 17/29* (2006.01)
*A61B 17/00* (2006.01)

(52) U.S. Cl.
CPC ...... *A61B 18/1445* (2013.01); *A61B 17/2909* (2013.01); *A61B 2017/0046* (2013.01); *A61B 2017/2901* (2013.01); *A61B 2017/2912* (2013.01); *A61B 2017/2929* (2013.01)

(58) Field of Classification Search
CPC ............ A61B 17/2909; A61B 18/1445; A61B 2017/0046; A61B 2017/2901; A61B 2017/2929; A61B 2017/2912
USPC ...................................... 606/41–50
See application file for complete search history.

(56) References Cited

U.S. PATENT DOCUMENTS

| 5,174,300 A * | 12/1992 | Bales ..................... A61B 17/29 294/115 |
| 5,344,428 A * | 9/1994 | Griffiths ................. A61B 17/29 600/564 |
| 6,032,849 A * | 3/2000 | Mastri ............. A61B 17/07207 227/176.1 |
| 6,117,158 A * | 9/2000 | Measamer ......... A61B 17/2909 606/208 |

FOREIGN PATENT DOCUMENTS

| DE | 20309776 U1 | 10/2003 |
| TW | M382110 U1 | 6/2010 |
| TW | 201414950 A | 4/2014 |

* cited by examiner

*Primary Examiner* — Michael Peffley

(57) ABSTRACT

An electrocautery instrument for endoscopic therapy includes an operation handle and a rotatable positioning means. The operation handle includes a cylindrical member, a fastening element, and a fixing protruding element. The fastening element and the fixing protruding element are disposed on the cylindrical member which further has a first inner hole. The rotatable positioning means encloses the cylindrical member and includes a rotatable element, a second inner hole, a clasping member, and securing units. The clasping member is disposed on a side wall of the second inner hole and engages with the fastening element. The rotatable element is provided for rotating the rotatable positioning means, so that the fixing protruding element can be positioned on any corresponding securing unit. Therefore, an electrocautery rod can be connectedly moved with the operation handle, thereby reducing components of the electrocautery instrument, and thus the cost is reduced greatly.

14 Claims, 6 Drawing Sheets

ELECTROCAUTERY INSTRUMENT FOR ENDOSCOPIC THERAPY

BACKGROUND

1. Technical Field

The present invention relates to an electrocautery instrument, and, in particular, to a disposable-type electrocautery instrument for endoscopic therapy.

2. Related Art

In recent years, surgical operations is moving toward the minimally invasive surgery (MIS) which allows smaller operative trauma during operations. Compared to conventional techniques, the MIS has features such as a small operative cut, a small operative trauma, fast recovery, and less pain.

Taking the endoscopic MIS as an example, various long-handled instruments are adopted during the surgical operations in order for the surgeon to perform cutting, trimming, clamping, and other actions in a small room, wherein the electrosurgical units (ESU) are used with minimally invasive electrocautery instruments such as scissors and a clamp. The tips of the electrocautery instruments discharge high-frequency electrical currents to surgical portions such as blood vessels, muscles, or tissues to perform surgical treatments such as electrocautery cutting, burning to stop bleeding, stripping, clipping, stitching up, knotting, or trimming.

In consideration of hygiene and safety, electrocautery instruments are disposable like traditional needles, that is to say, they are designed to be used once and then abandoned. However, in the current market, the electrocautery instruments for the endoscopic MIS have too many components and parts, which causing inconvenience in assembly and demanding a lot of manufacturing modules. In other words, having too many components and parts means that many manufacturing modules are required, assembling procedures are complicated, and automated production is in low level, which consequently leading to a high manufacturing cost and complicated assembly.

In view of the foregoing, industries in the related fields aim to solve the problems of the high manufacturing cost and the complicated assembly.

BRIEF SUMMARY

It is an object of the present invention to provide an electrocautery instrument for endoscopic therapy, wherein it can achieve the same effects as electrocautery tools while its components are reduced to the least possible number, thereby reducing assembly procedures and manufacturing costs greatly.

It is another object of the present invention to provide an electrocautery instrument for endoscopic therapy, which has a simplified structure and a reduced assembly time, and easily achieves automated assembly and production.

Accordingly, the present invention provides an electrocautery instrument for endoscopic therapy, for use with an electrocautery rod. The electrocautery instrument for endoscopic therapy comprises an operation handle and a rotatable positioning means. The operation handle includes a cylindrical member, a fastening element, and at least one fixing protruding element. The fastening element and the fixing protruding element are disposed on the cylindrical member which further has a first inner hole. The rotatable positioning means encloses the cylindrical member and further comprises a rotatable element, a second inner hole, at least one clasping member, and a plurality of securing units. The rotatable element is rotatably connected with the cylindrical member. The clasping member is disposed on a side wall of the second inner hole and engages with the fastening element. Each of the securing units is recessed in the side wall of the second inner hole, wherein the rotatable element is disposed corresponding to the fixing protruding element. The rotatable element is provided for rotating the rotatable positioning means, so that the fixing protruding element is positioned on any corresponding securing unit. The electrocautery rod penetrates through the second inner hole and the first inner hole for being connectedly moved with the operation handle.

The present invention further has the following effects: when a surgeon rotates the rotatable positioning means by his/her fingers, the fixing protruding element of the cylindrical member is brought into contact against the securing units, and thereby a tiny sound is generated and makes the surgeon has a better operation hand feeling. In addition, the present invention has a simplified structure with a low manufacturing cost, is disposable after being used once, and prevents superimposed infections, thereby protecting patients' life safety.

DETAILED DESCRIPTION

Detailed descriptions and technical contents of the present invention are illustrated below in conjunction with the accompany drawings. However, it is to be understood that the descriptions and the accompany drawings disclosed herein are merely illustrative and exemplary and not intended to limit the scope of the present invention.

Figure 1:
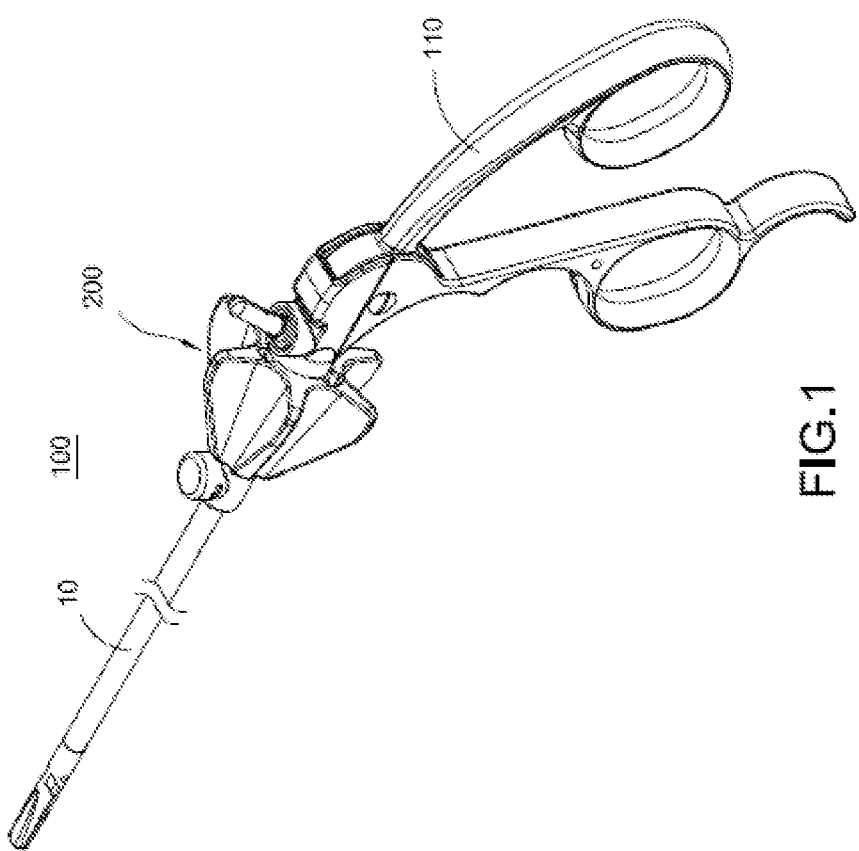
FIG. 1 is a schematic perspective view of an electrocautery instrument according to the present invention.

FIG. 1 is a schematic perspective schematic view of an electrocautery instrument 100 according to the present invention. The present invention provides an electrocautery instrument 100 for endoscopic therapy, for use with an electrocautery rod 10. The electrocautery rod 10 mentioned herein is only one embodiment of the present invention; however, in a different embodiment, it can be scissors, a clamp, or other suitable electrocautery tools. The electrocautery instrument 100 comprises an operation handle 110 and a rotatable positioning means 200.

Figure 2:
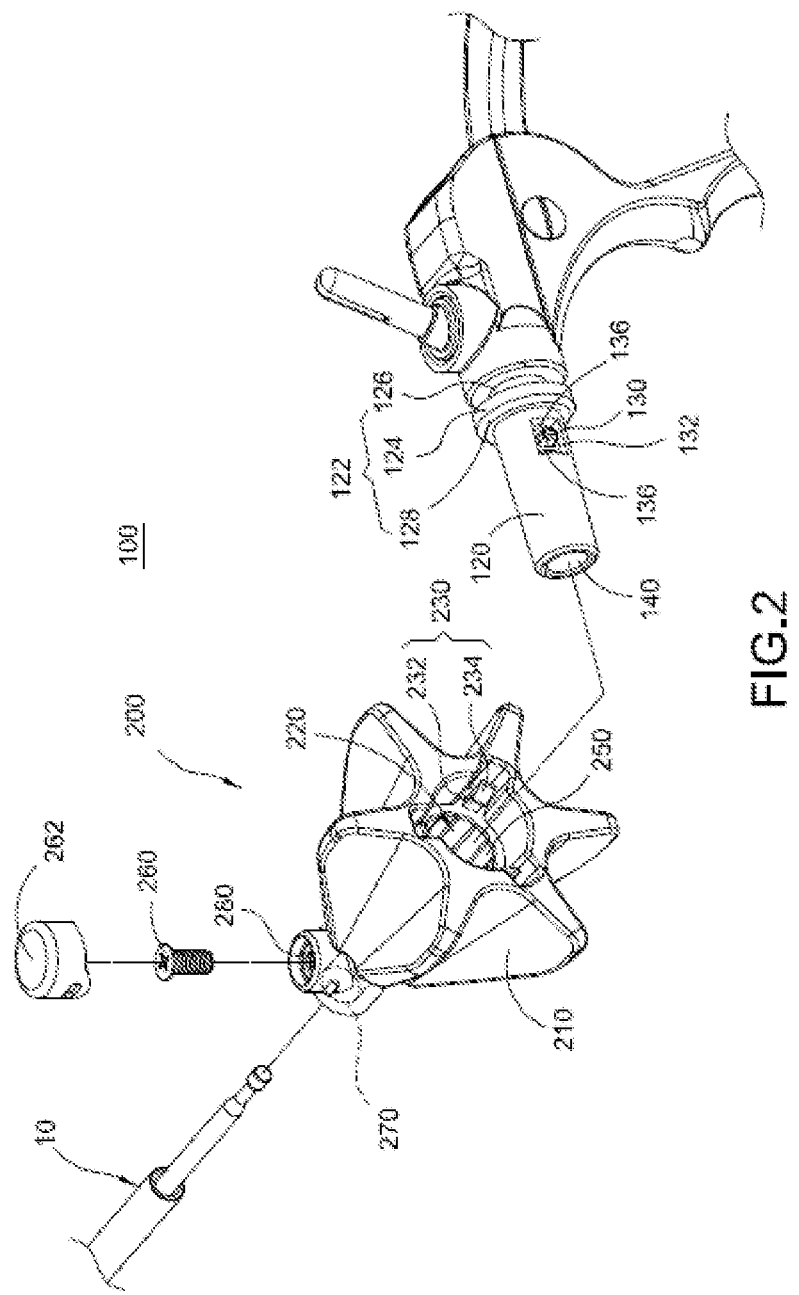
FIG. 2 is a schematic exploded view of the electrocautery instrument according to the present invention.
Figure 3:
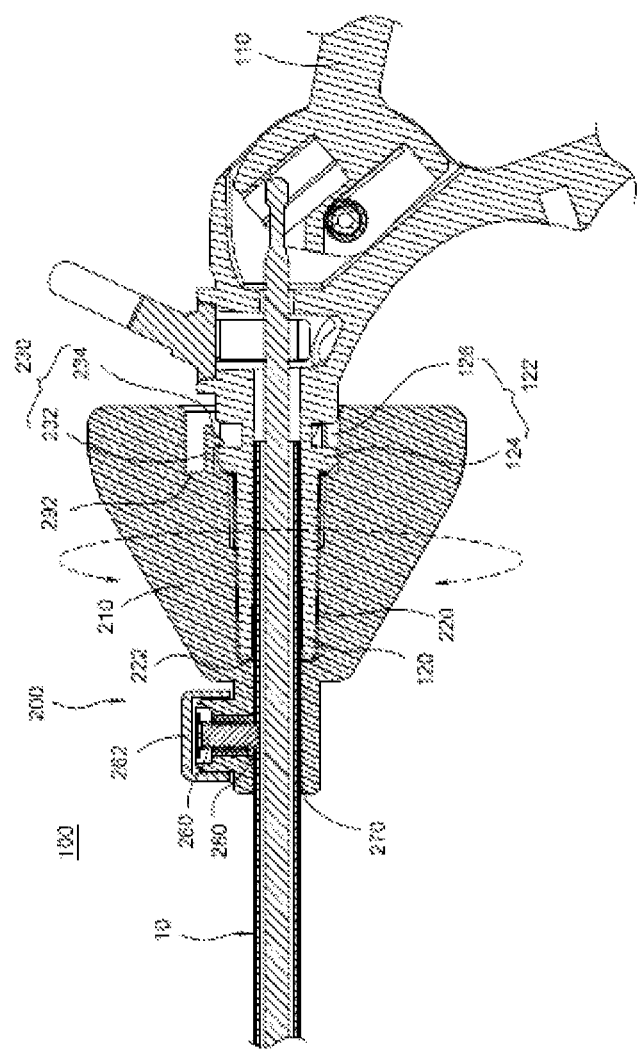
FIG. 3 is a cross-sectional view of the electrocautery instrument according to the present invention.

Referring to FIGS. 2 and 3. FIG. 2 is a schematic exploded view of the electrocautery instrument 100 according to the present invention. FIG. 3 is a cross-sectional view of the electrocautery instrument 100 according to the present invention. The operation handle 110 includes a cylindrical member 120, a fastening element 122, and at least one fixing protruding element 130. The fastening element 122 and the fixing protruding element 130 are disposed on an outer surface of the cylindrical member 120, wherein the cylindrical member 120 further forms a first inner hole 140 for the electrocautery rod 10 to penetrate therethrough. The fastening element 122 mentioned above further comprises a flange 124 and a notch 126. One side of the flange 124 forms a chamfer angle 128, and the flange 124 is adjacent to the notch 126. The fixing protruding elements 130 are preferably disposed on two sides of the cylindrical member 120 and protrude from a recess 132 formed on the cylindrical member 120, so that a top surface of each fixing protruding element 130 can protrude out of an outer surface of the cylindrical member 120.

The rotatable positioning means 200 encloses the cylindrical member 120. The rotatable positioning means 200 comprises a rotatable element 210, a second inner hole 220, at least one clasping member 230, and a plurality of securing units 250. The rotatable element 210 is rotatably connected to the cylindrical member 120 (a dotted line shown in FIG. 3 indicates a rotation direction of the rotatable element 210). The clasping member 230 is disposed on a side wall of the second inner hole 220 and engages with the fastening element 122. The securing units 250 are respectively adjacent to one another on and around the side wall of second inner hole 220.

Figure 4:
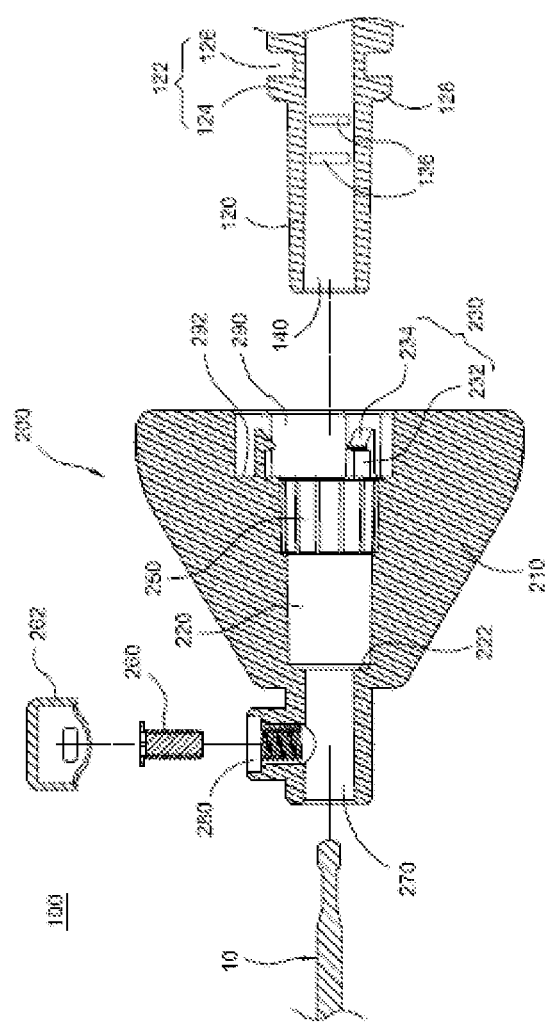
FIG. 4 is an exploded cross-sectional view of the electrocautery instrument according to the present invention.

Please refer to FIG. 4, which is an exploded cross-sectional view of the electrocautery instrument 100 according to the present invention. The clasping member 230 is disposed in a fourth inner hole 290 communicates with the second inner hole 220. The rotatable positioning means 200 further comprises a positioning element 260, a third inner hole 270, a through hole 280, and a base 292. The rotatable positioning means 200 includes three inner holes which were in a ladder-like distribution thereinside, and the three inner holes are the second inner hole 220, the third inner hole 270, and the fourth inner hole 290. In addition, the second inner hole 220, the third inner hole 270, and the fourth inner hole 290 communicate with one another, and are preferably placed on the same axis; however, in other embodiments, they don't have to be placed on the same axis, the arrangement can change as required, and the present invention is not limited to the described arrangement.

During a process that the rotatable positioning means 200 encloses the cylindrical member 120, the cylindrical member 120 can only be assembled until it abuts against a circular baffle 222 at a boundary between the third inner hole 270 and the second inner hole 220. In other words, when assembling the rotatable positioning means 200 and the operation handle 110, the cylindrical member 120 enters into the fourth inner hole 290 and the second inner hole 220 sequentially but does not enter into the third inner hole 270.

Moreover, the diameter of the third inner hole 270 is smaller than the diameter of the second inner hole 220. The second inner hole 220 is formed between the fourth inner hole 290 and the third inner hole 270, and the diameter of the fourth inner hole 290 is greater than the diameter of the second inner hole 220. The diameter of the first inner hole 140 is between the diameter of the second inner hole 220 and the diameter of the third inner hole 270.

The base 292 of the fourth inner hole 290 is further perpendicular to a side wall of the fourth inner hole 290. The clasping member 230 protrudes perpendicularly from the base 292 into the fourth inner hole 290 and engages with the fastening element 122 of the cylindrical member 120.

Figure 5:
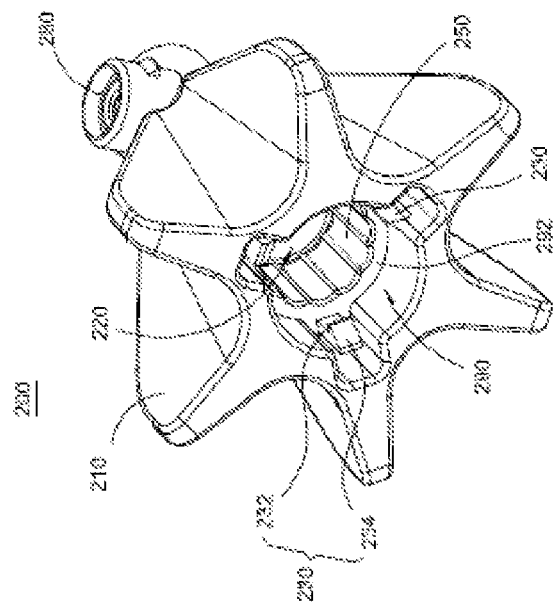
FIG. 5 is a schematic perspective view of a rotatable positioning means according to the present invention.

FIG. 5 is a schematic perspective view of the rotatable positioning means 200 according to the present invention. The clasping member 230 further has an extending arm 232 and a hook 234, wherein the hook 234 is disposed on one end of the extending arm 232, so that after the rotatable positioning means 200 encloses the cylindrical member 120, the extending arm 232 can make the hook 234 elastically engaged with the fastening element 122. More specifically, when the rotatable positioning means 200 is to enclose the cylindrical member 120, the hook 234 likewise having an inclined surface (not labelled in the drawing) passes the flange 124 having a chamfer angle 128, and then only a very small force is required to make the hook 234 of the clasping member 230 elastically go across the flange 124 to engage the notch 126.

In the preferable embodiment of the present invention, the number of the clasping members 230 may be three. When the rotatable positioning means 200 encloses the cylindrical member 120, the three clasping members 230 may be stably fixed on the cylindrical member 120. However, the number of the clasping member 230 varies as required, and is not limited to the disclosures of the present invention. Therefore, when the rotatable positioning means 200 is assembled on the cylindrical member 120 of the operation handle 110, the assembly is convenient and simple and prevents becoming loosened or detached.

It should be noted that one of the technical features of the present invention is that the through hole 280 is formed on one lateral edge of the rotatable positioning means 200, and the through hole 280 communicates with the third inner hole 270 (as shown in FIG. 4) for the positioning element 260 to penetrate through, wherein the positioning element 260 can be one of a screw, a bolt, a pin, and a key. In the preferable embodiment of the present invention, the positioning element 260 is the screw that can enhance positioning and fixing the electrocautery rod 10 or can allows easy detachment of the electrocautery rod 10. In other words, the positioning element 260 disposed in a radial direction (not illustrated) of the third inner hole 270 can assistedly position the electrocautery rod 10 in the radial direction.

Figure 6:
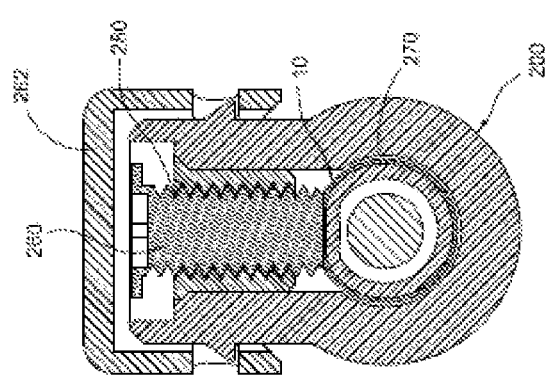
FIG. 6 is a cross-sectional view illustrating that the positioning element positions an electrocautery rod according to the present invention.

When the positioning element 260 is the screw, please refer to FIG. 6 which is a cross-sectional view illustrating that the positioning element 260 positions the electrocautery rod 10 according to the present invention. A through hole 280 is formed in the radial direction (not illustrated) of the third inner hole 270, and the threaded positioning element 260 is screwed into the through hole 280 to penetrate therethrough and makes contact against the electrocautery rod 10, so as to assistedly position the electrocautery rod 10 in the radial direction. As the embodiment shown in FIG. 3, FIG. 4, and FIG. 6, the positioning element 260 further has a cover 262 positioned at an upper end of the through hole 280, so as to prevent the positioning element 260 from moving in the radial direction (not illustrated).

Figure 7:
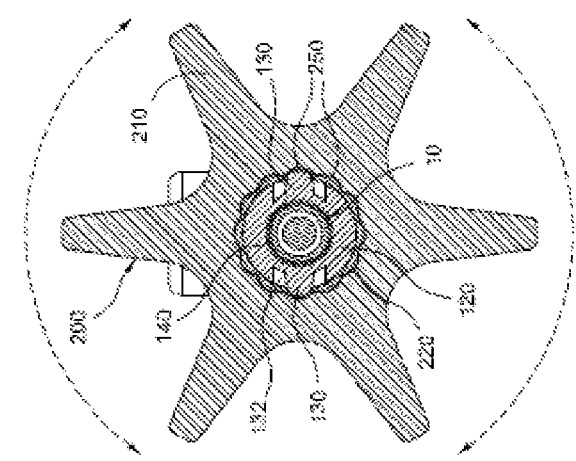
FIG. 7 is a cross-sectional view illustrating that each fixing protruding element is disposed corresponding to a respective securing unit according to the present invention.

Please refer to FIG. 7 which shows a cross-sectional view illustrating that each fixing protruding element 130 is disposed corresponding to a respective securing unit 250 according to the present invention. Each of the securing units 250 is adjacently disposed on and around the side wall of the second inner hole 220 and is disposed corresponding to each of the fixing protruding elements 130. Also referring to FIGS. 2 to 4, a pair of penetrating holes 136 are formed on two sides of the fixing protruding element 130, and the pair of the penetrating holes 136 are located in the recess 132. Each of the penetrating holes 136 further communicates with the first inner hole 140 of the cylindrical member 120. By this design, each fixing protruding elements 130 on the cylindrical member 120 has elasticity to such a degree that each fixing protruding element 130 can elastically move a little under an external force.

After the rotatable positioning means 200 is assembled on the cylindrical member 120, the rotatable element 210 is disposed corresponding to each fixing positioning element 130. In other words, after the rotatable positioning means 200 is rotated by using the rotatable element 210, the fixing protruding element 130 is positioned on any corresponding securing unit 250. Each securing unit 250 is preferably in an arc shape. However, in different embodiments, the securing unit 250 can be in a semicircular shape, a trapezoid shape, or any other suitable shape.

Since the top surface of each fixing protruding element 130 protrudes out of the outer surface of the cylindrical member 120, the fixing protruding element 130 makes contact with each securing unit 250, and thereby the rotatable element 210 can easily rotate. As shown in FIG. 7, the length (i.e. the length of the arc shape) of each securing unit 250 is preferably equal to the length of each fixing protruding element 130, so that each of the fixing protruding elements 130 is positioned on a corresponding securing unit 250. Therefore, when a surgeon rotates the rotatable positioning means 200 by his/her fingers, each fixing protruding element 130 of the cylindrical member 120 is brought into elastic contact with the securing units 250, thereby generating a tiny sound that makes the surgeon have a better operation (positioning) hand feeling.

Finally, the electrocautery rod 10 penetrates through the third inner hole 270, the second inner hole 220, the fourth inner hole 290, and the first inner hole 140 in sequence, and such that the electrocautery rod 10 can be connectedly moved with the operation handle 110. Therefore, the electrocautery instrument 100 of the present invention has a simplified structure with a low manufacturing cost and is disposable after being used once.

It should be noted that the rotatable element 210 of the present embodiment is preferably constituted by a plurality of protruding portions. However, in other embodiments, the rotatable element 210 can be, for example, a frictional element having patterns on its outer surface, an adjusting element having a ratchet or a gear, or other proper elements that can make the rotatable element 210 of the present embodiment rotate properly.

In summary, the electrocautery instrument for endoscopic therapy according to the present invention certainly can achieve the anticipated objects and improve the defects of the traditional techniques, and has novelty and non-obviousness, so the present invention completely meet the requirements of patentability. Therefore, a request to patent the present invention is filed according to patent laws. Examination is kindly requested, and allowance of the present application is solicited to protect the rights of the inventor.

What is claimed is:

1. An electrocautery instrument used in endoscopic therapy and collaborating with an electrocautery rod, comprising:
   an operation handle including a cylindrical member, a fastening element, and at least one fixing protruding element, the fastening element and the fixing protruding element being disposed on the cylindrical member, wherein the cylindrical member further includes a first inner hole; and
   a rotatable positioning means enclosing the cylindrical member, the rotatable positioning means further including a rotatable element, a second inner hole, at least one clasping member, and a plurality of securing units, the rotatable element being rotatably connected to the cylindrical member, the at least one clasping member being disposed on a side wall of the second inner hole and engaged with the fastening element, the securing units being respectively recessed in the side wall of the second inner hole, wherein the rotatable element is disposed corresponding to the at least one fixing protruding element, the rotatable element is provided for rotating the rotatable positioning means, so that the at least one fixing protruding element is positioned on any one of the corresponding securing units, and the electrocautery rod penetrates through the second inner hole and the first inner hole respectively for being connectedly moved with the operation handle.

2. The electrocautery instrument of claim 1, wherein the rotatable positioning means further comprises a positioning element, a third inner hole, and a through hole, the third inner hole communicates with the second inner hole, the through hole is formed on the rotatable positioning means and communicates with the third inner hole, wherein the diameter of the third inner hole is smaller than the diameter of the second inner hole, and the positioning element is disposed in the through hole in a radial direction of the third inner hole for assistedly positioning the electrocautery rod in the radial direction.

3. The electrocautery instrument of claim 2, wherein a fourth inner hole is further formed in the rotatable positioning means, wherein the second inner hole is formed between the fourth inner hole and the third inner hole, and when the rotatable positioning means encloses the cylindrical member, the cylindrical member enters the fourth inner hole and the second inner hole in sequence but does not enter the third inner hole.

4. The electrocautery instrument of claim 2, wherein the diameter of the first inner hole is between the diameter of the second inner hole and the diameter of the third inner hole.

5. The electrocautery instrument of claim 2, wherein the positioning element includes one of a screw, a bolt, a pin, and a key.

6. The electrocautery instrument of claim 1, wherein the fastening element further comprises a flange and a notch, a chamfer angle is formed on one side of the flange, and the flange is adjacent to the notch.

7. The electrocautery instrument of claim 6, wherein the clasping member is across the flange having the chamfer angle and engaged in the notch.

8. The electrocautery instrument of claim 6, wherein the rotatable positioning means further forms a fourth inner hole and a base, the diameter of the fourth inner hole is greater than the diameter of the second inner hole, the base is perpendicular to a side wall of the fourth inner hole, and the at least one clasping member perpendicularly protrudes from the base into the fourth inner hole and engages with the fastening element.

9. The electrocautery instrument of claim 1, wherein the cylindrical member further forms a recess, the at least one fixing protruding element protrudes from the recess, and a top surface of the at least one fixing protruding element protrudes out of an outer surface of the cylindrical member.

10. The electrocautery instrument of claim 9, wherein a pair of penetrating holes is formed in the recess, and the pair of penetrating holes is formed at two sides of the fixing protruding element respectively and communicates with the first inner hole.

11. The electrocautery instrument of claim 1, wherein the at least one clasping member includes an extending arm and a hook, the hook is disposed on one end of the extending arm, and the extending arm is elastically movable to engage the hook with the fastening element.

12. The electrocautery instrument of claim 1, wherein the plurality of securing units respectively adjacently disposed on and around the side wall of the second inner hole, and the length of each of the plurality of securing units is equal to the length of the at least one positioning protruding element.

13. The electrocautery instrument of claim 12, wherein the shape of each of the plurality of securing units includes an arc shape, a semicircular shape, or a trapezoid shape.

14. The electrocautery instrument of claim 1, wherein the rotatable element comprises a plurality of protruding portions, a frictional element, or an adjusting element.

* * * * *